United States Patent [19]

Brickl et al.

[11] 4,427,648

[45] Jan. 24, 1984

[54] DIPYRIDAMOLE-CONTAINING PHARMACEUTICAL FORM

[75] Inventors: Rolf Brickl, Warthausen; Peter Gruber, Biberach; Gottfried Schepky, Biberach; Gerhard Bozler, Biberach, all of Fed. Rep. of Germany

[73] Assignee: Dr. Karl Thomae GmbH, Biberach an der Riss, Fed. Rep. of Germany

[21] Appl. No.: 389,282

[22] Filed: Jun. 17, 1982

[30] Foreign Application Priority Data

Jun. 19, 1981 [DE] Fed. Rep. of Germany ....... 3124090

[51] Int. Cl.$^3$ ............... A61K 9/00; A61K 9/20; A61K 9/48; A61K 31/445
[52] U.S. Cl. ............... 424/16; 424/19; 424/20; 424/21; 424/22; 424/32; 424/35; 424/37; 424/38; 424/251; 424/267
[58] Field of Search ............... 424/19–22, 424/32, 35, 37, 38, 251, 267

[56] References Cited

U.S. PATENT DOCUMENTS

| | | | |
|---|---|---|---|
| 4,361,546 | 11/1982 | Stricker et al. | 424/19 |
| 4,367,217 | 1/1983 | Gruber et al. | 424/19 |

FOREIGN PATENT DOCUMENTS 2039737 8/1980 United Kingdom.

*Primary Examiner*—Shep K. Rose
*Attorney, Agent, or Firm*—Hammond & Littell, Weissenberger & Muserlian

[57] ABSTRACT

This invention relates to vehicles for the administration of dipyridamole. More specifically, this invention relates to a method of treating cardiovascular disorders in a host in need of such treatment which comprises administering to said host a cardiovascularly effective amount of a composition comprised of (i) dipyridamole or an acid addition salt thereof and (ii) at least one pharmacologically acceptable acid or acid substance, the total amount of acid from acid addition salt present and acid or acid substance being in a ratio of at least about 5 acid equivalents to 1 mol of dipyridamole, preferably in the form of particles having particle sizes of from about 0.1 to 2.0 mm.

22 Claims, 6 Drawing Figures

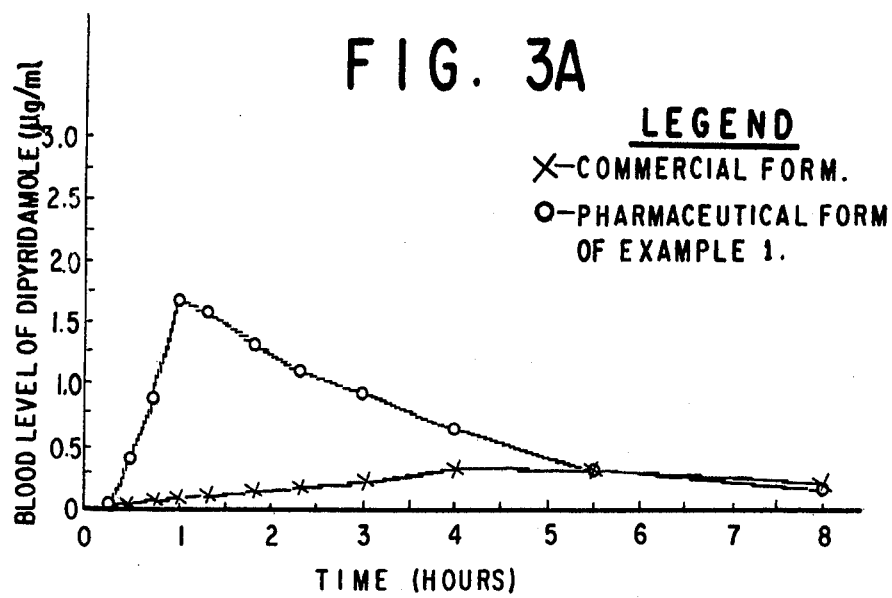
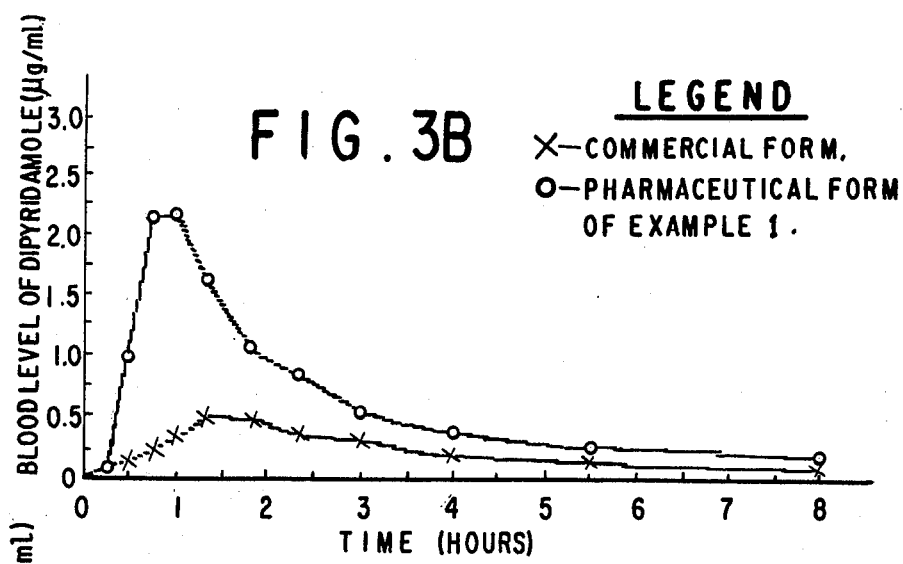
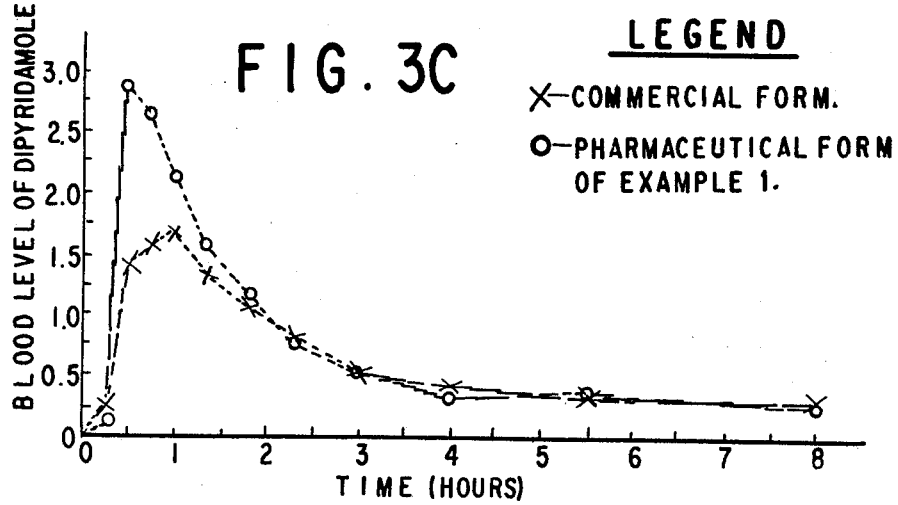

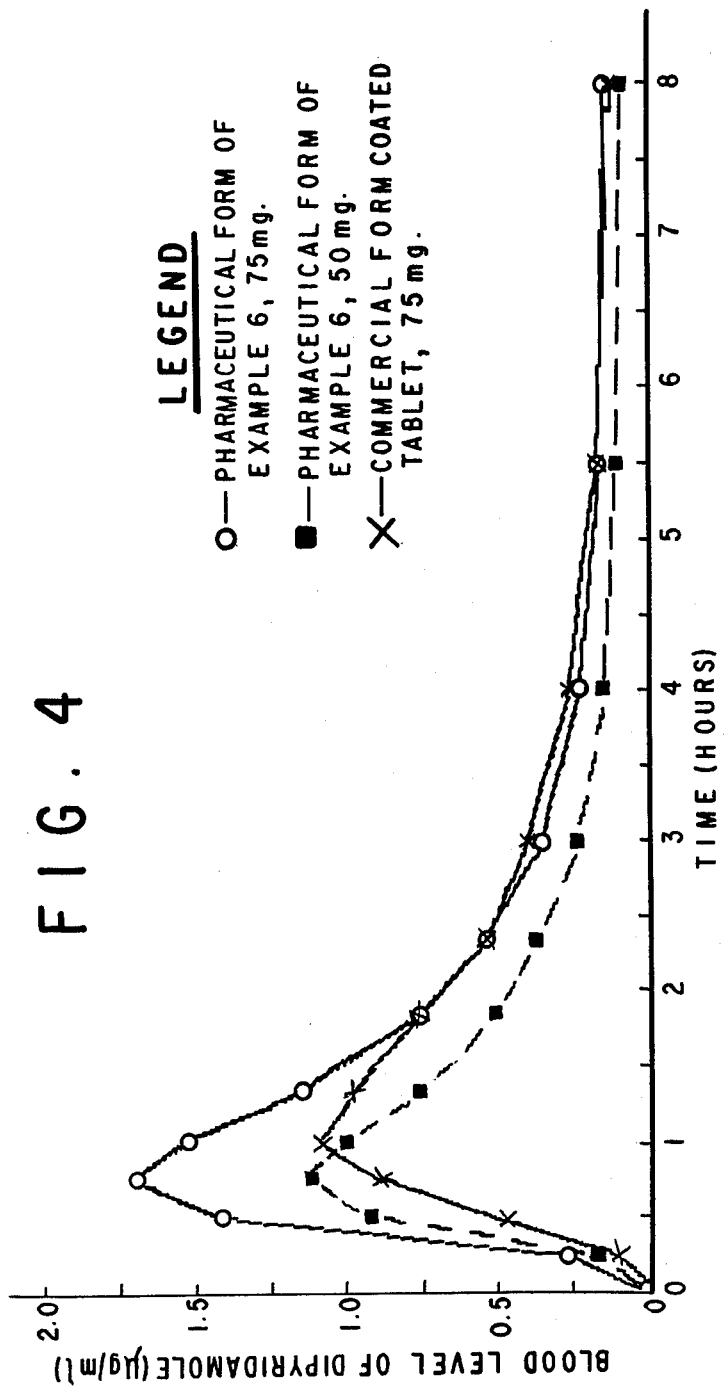

not present.  No special capacity (empty by design).

DIPYRIDAMOLE-CONTAINING PHARMACEUTICAL FORM

FIELD OF THE INVENTION

This invention relates to vehicles for the administration of dipyridamole. More specifically, this invention relates to a dipyridamole-containing pharmaceutical form with a relative bioavailability of more than 100%, as compared to dipyridamole solutions, and the use of said pharmaceutical form in treating cardiovascular disorders.

BACKGROUND OF THE INVENTION

The compound 2,6-bis-(diethanolamino)-4,8-dipiperidinopyrimido[5,4-d]pyrimidine, known as dipyridamole, is disclosed in U.S. Pat. No. 3,031,450, incorporated herein by reference. This compound has been successfully used as an active substance, such as a coronary vasodilator, for many years. The pharmaceutical preparations previously known which contain this active substance have a number of disadvantages for certain applications due to the special physical properties of dipyridamole.

Dipyridamole is readily water-soluble only in an acidic medium, and therefore it can only go into solution from solid pharmaceutical forms and then be absorbed if the pharmaceutical preparations remain in the acidic range for a sufficiently long period. Thus, the solubility and hence also the absorption greatly depend upon the retention time and the pH value in the stomach and upper intestinal tract. This results in sharp inter-individual and intra-individual fluctuations in the blood levels (see Table 3 below) since the motility of a patent, the pH of the patient's stomach and intestines, and the patient's food intake have a considerable influence on absorption. In some patients the blood levels may even be so low that they practically amount to an absence of absorption.

OBJECTS OF THE INVENTION

It is an object of the invention to provide vehicles for administering dipyridamole.

It is also an object of the invention to provide dipyridamole-containing pharmaceutical forms with a relative bioavailability of more than 100%, as compared to dipyridamole solutions, and a method for their use.

It is a further object of the invention to provide a method of treating cardiovascular disorders in a host in need of such treatment which comprises administering to said host a cardiovascularly effective amount of a composition comprised of (i) dipyridamole or an acid addition salt thereof and (ii) at least one pharmacologically acceptable acid or acid substance, the total amount of acid from acid addition salt present and acid or acid substance being in a ratio of at least about 5 acid equivalents to 1 mol of dipyridamole.

These and other objects of the invention will become more apparent in the discussion below.

BRIEF DESCRIPTION OF THE DRAWINGS

FIGS. 3A to 3C represent comparisons of the release characteristics of a known form for administering dipyridamole and of an embodiment of the invention in each of three test subjects.

FIG. 4 represents a comparison of the release characteristics of two embodiments of the invention and of a known form for administering dipyridamole.

Figure 1:
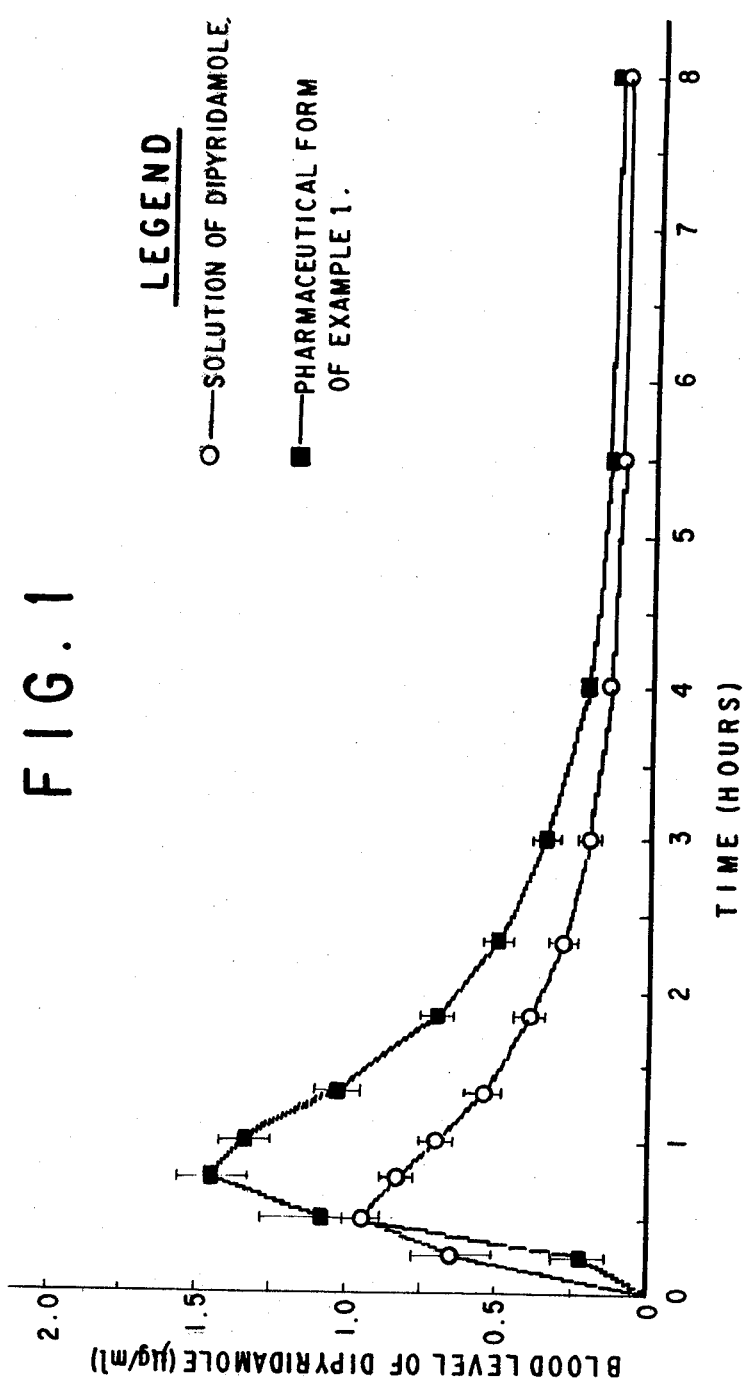
FIG. 1 represents a comparison of the release characteristics of a dipyridamole-containing solution and of an embodiment of the invention.

The release characteristics are shown by blood-level curves.

DETAILED DESCRIPTION OF THE INVENTION

Applicants have developed a novel dipyridamole-containing pharmaceutical form which is characterized by exhibiting a relative bioavailability greater than 100%, as compared with dipyridamole solutions, and substantially lower inter-individual and intra-individual fluctuations in blood level. These novel pharmaceutical preparations represent particular pharmokinetic advantages over previously known pharmaceutical forms.

More specifically, the pharmaceutical form of this invention is comprised of (i) dipyridamole or an acid addition salt thereof and (ii) at least one pharmacologically acceptable acid or acid substance, the total amount of acid from acid addition salt present and acid or acid substance being in a ratio of at least about 5 acid equivalents to 1 mol of dipyridamole, preferably in the form of particles having particle sizes of from about 0.1 to 2.0 mm. Other, conventional additives may optionally be present. This dipyridamole preparation is characterized in that, irrespective of the physiological conditions in the gastrointestinal tract—for example, irrespective of the pH, the buffering effect and the motility of this tract—it results in a high reproducible bioavailability of the dipyridamole.

An acidic dipyridamole solution should be the best form of administration per se since the active substance is given in dissolved form; one would expect total absorption together with a very high bioavailability. Accordingly, the quality of a pharmaceutical preparation is usually given in terms of its relative bioavailability as compared to a solution of the active substance. For this purpose, the area under the blood level curve (AUC) for the particular pharmaceutical preparation is determined and then compared with that of the solution (100%). However, it has totally unexpectedly been found that the relative bioavailability of dipyridamole is above the theoretically possible limit of 100%, corresponding to use of an acidic dipyridamole solution, namely, in the range of 140 to 150%, when the solid forms according to the invention are used.

Tests with radioactively labelled dipyridamole wherein the substance was given once intravenously, as an acidic solution, and another time orally, as an acidic solution, have lead to the conclusion that even when dipyridamole is administered in dissolved form to the body, it is not absorbed totally but only to about 60 to 70%. This absorption quota can be determined not only from a comparison of the urine precipitation for both types of administration but also from clearance calculations.

In published British Patent Application No. 2,039,737A, Example 8 describes a granulate consisting of 0.5 kg of dipyridamole and 0.25 kg of fumaric acid and the preparation thereof. One mol of dipyridamole is used for four equivalents of fumaric acid. When this example was repeated, a dipyridamole granulate of which the pH-independent solubility was totally unsatisfactory even though the fumaric acid was present in an excess of one mol of dipyridamole to four equivalents of fumaric acid, was obtained. Also, as can be seen from FIG. 2 of the above-mentioned British patent application, the release of active substance is only 10% after one hour and reaches about 100% only after 6 hours. This, and the method of production described therein, show that this is a delayed release form for dipyridamole. The pharmaceutical preparations according to the invention differ in that after about 30 minutes to 2 hours after administration, they result in highly reproducible blood levels with the maximum bioavailability.

The pharmaceutical forms according to the invention are further distinguished in that they contain an intimate mixture of dipyridamole or an acid addition salt thereof and an excess in the ratio of 1 mol of dipyridamole to a total of at least about 5 acid equivalents of acid from acid addition salt present and pharmacologically acceptable acid or acid substance (referred to collectively hereinafter as "acid present"). It was not to be expected that a further excess of said would suddenly lead to a significant increase in the bioavailability of the dipyridamole.

The dependency of the solubility or speed of dissolution of the dipyridamole upon the quantity of acid added thereto has been investigated for different dosages. The two tables below show this dependence as it relates to dipyridamole-containing film-coated tablets also containing differing amounts of tartaric acid or fumaric acid per tablet. The tablets were tested in vitro using the USP-XX-paddle method at 100 rpm in 500 ml of dilute McIlvain buffer with a pH of 6.

TABLE 1

Percentage release in vitro from film-coated tablets containing 75 mg of dipyridamole each and various amounts of fumaric acid in dilute buffer solution (pH 6)

| Amount of Fumaric Acid (mg/tablet) | Acid Equivalents per 1 mol of Dipyridamole | Percent of Dipyridamole Released | |
|---|---|---|---|
| | | After 5 minutes | After 10 minutes |
| 0 | — | 7 | 7 |
| 30 | 3.5 | 17 | 27 |
| 60 | 6.9 | 37 | 60 |
| 120 | 13.8 | 53 | 77 |
| 180 | 20.7 | 66 | 85 |

TABLE 2

Percentage release in vitro from film-coated tablets containing 75 mg of dipyridamole each and various amounts of tartaric acid in dilute buffer solution (pH 6)

| Amount of tartaric acid (mg/tablet) | Percent of Dipyridamole Released | |
|---|---|---|
| | After 10 minutes | After 30 minutes |
| 0 | 7 | 7 |
| 10 | 13 | 13 |
| 20 | 21 | 21 |
| 30 | 35 | 40 |
| 40 | 33 | 50 |
| 80 | 39 | 68 |

It was not foreseeable that dipyridamole which was present in only relatively small absolute quantities and was totally dissolved should form strongly supersaturated solutions with a concentration up to 20 times the true solubility and that this phenomenon should occur particularly if there are more than about 5 acid equivalents of acid present per mol of dipyridamole. In vivo tests with the pharmaceutical forms according to the invention have shown that, as compared with acidic solutions, a bioavailability of about 150% is achieved when the forms according to the invention are used (see FIGS. 1 and 2). A further advantage of these forms is that, due to the pH-independent solubility, the release profile and hence also the blood levels can be controlled without any loss in bioavailability.

The extremely surprising discovery of the increase in relative bioavailability to about 150% as compared with a solution may possibly arise from the fact that supersaturated and more highly concentrated solutions of active substance are formed. When dipyridamole is administered in dissolved form, it is not impossible that some of the active substance may have already precipitated out of the solution in the upper section of the intestines, before being completely absorbed, which surprisingly would appear not to happen with supersaturated solutions. It must be remembered that, during the transition from the acidic stomach to the intestines, the solubility of the dipyridamole decreases by a factor of far more than 1000 and, at pH 7.0, for example, the solubility of dipyridamole is only about 1 mg per liter. At a pH of about 4.0, the solubility of dipyridamole is already so low that there would virtually be no absorption that is, virtually no level of dipyridamole in the blood.

Since dipyridamole is a substance with a reversible effect, i.e., its therapeutic effect lasts only as long as the blood levels are kept sufficiently high, use of the dipyridamole-containing pharmaceutical forms according to the invention results in a further improvement in the therapeutic activity. Thus, as a whole, use of the pharmaceutical forms according to the invention has the following advantages over use of conventional preparations:

1. Higher bioavailability.
2. Higher therapeutic reliability, which is achieved by the fact that, on the one hand, the inter-individual and intra-individual fluctuations which are typical of known forms are reduced and, on the other hand, totally inadequate blood level values are avoided (for example, in patients who normally only barely resorb dipyridamole; see FIG. 3A).
3. By control of the release, it is possible to improve the therapeutic effect and avoid side-effects at higher doses (see FIG. 2).
4. In some cases the higher bioavailability makes it possible to reduce the dosage (FIG. 4 shows that a reduction of the dose to 50 mg still yields a bioequivalent form).

It has been found that the remarkable increase in the relative bioavailability of dipyridamole can be achieved with a variety of pharmaceutical forms for oral administration. The essential prerequisite for the high blood levels is the determination of the correct ratio of acid present to dipyridamole.

Extensive tests have shown that at least about 5 acid equivalents of acid present to 1 mol of dipyridamole are required to obtain a significant improvement in the bioavailability of dipyridamole. The quantity of acid present in relation to the dipyridamole has no upper limit per se; it is only limited by the fact that if the quantity of acid present is too great, it is not possible to produce an oral form of dipyridamole which can be easily swallowed. A ratio of from about 10 to 30 acid equivalents of acid present to 1 mol of dipyridamole is preferred.

The acid addition salts of dipyridamole comprise pharmacologically acceptable reaction products of dipyridamole and inorganic or organic acids. Suitable such acids, which are well known to those skilled in the art, include hydrochloric acid, tartaric acid, and citric acid.

Useful acids or acid substances, that is, acidic excipients, comprise a plurality of toxicologically harmless, that is, pharmacologically acceptable, acids or acid substances. Suitable acids include, for example, fumaric acid, malic acid, tartaric acid, citric acid, succinic acid, ascorbic acid, adipic acid, and mixtures of any two or more of these acids. Suitable acid substances include monopotassium or monosodium salts of the aforementioned acids, such as, for example, monopotassium citrate or monopotassium tartarate, and acid salts selected from the group consisting of, for example, sodium or potassium hydrogen sulfate, betaine hydrochloride, and the like. Occasionally, anhydrides such as succinic anhydride, glutaric anhydride, or D-glucuronic acid-γ-lactone, which hydrolyze in the presence of water to form acids, may be used to increase the solubility of the dipyridamole. Preparations containing fumaric acid, which are distinguished by their long shelf life, are preferred.

The ease with which optimum solid dipyridamole preparations for oral administration can be produced was not foreseeable and was a complete surprise to anyone skilled in the art. According to the invention, preferred forms of dipyridamole are produced, for example, by simply mixing dipyridamole and fumaric acid together, with or without binders, and then compressing the mixture by means of tablet presses or roller compactors. The compressed masses are then broken up again by use of dry granulation equipment, and the resulting granules are transferred into hard gelatin capsules. The quantity of acidic excipients, the nature of these excipients, and the spectrum of particle sizes of the dry granulate are critical in achieving the optimum blood levels. In addition, dipyridamole may be pelleted together with acidic excipients, and the pellets are sorted out and transferred into hard gelatin capsules.

The particle sizes of dipyridamole-containing particles according to the invention are from about 0.1 to 2.0 mm, preferably from about 0.5 to 1.0 mm. This includes, for example, granules having particle sizes of from about 0.1 to 2.0 mm, preferably from about 0.25 to 1.25 mm, as well as pellets having particle sizes, that is, diameters, of from about 0.1 to 2.0 mm, preferably from about 0.5 to 1.5 mm.

Prior to insertion into hard gelatin capsules, dipyridamole-containing granules or pellets can be coated with a lacquer coating which releases at least 90% of the active substance over a period of 2 hours in the gastrointestinal tract.

The active substance may also be combined with the acidic excipient and other additives which can be used directly in tablets and with the lubricant to form a mixture which can be made directly into tablets. This mixture is then compressed to form tablet cores which are subsequently covered with a coating to mask the flavor or a lacquer coating which releases at least 90% of the active substance over a period of 2 hours in the gastrointestinal tract.

The active substance may also first be granulated with one or more acidic excipients, in a moist or dry state, and after the addition of further excipients, the granules are compressed to form tablet cores. However, it is also possible to convert the active substance and conventional excipients and a lubricant. Only then is the mass compressed to form tablet cores.

With respect to coatings, a flavor-masking coating may comprise any of the known pharmaceutically acceptable coatings such as, for example, hydroxypropyl methylcellulose. Suitable lacquer coatings include hydroxypropyl methylcellulose phthalate, copolymers of methacrylic acid and methacrylic acid ester, and mixtures thereof. The coatings may be present in amounts of from about 1 to 30% by weight, preferably from about 2 to 20% by weight, based upon the total weight of the coated granulate, pellets, or tablets.

Fumaric acid has proven to be a particularly suitable acid. It is physiologically non-toxic and easy to compress, and when combined with dipyridamole, it does not produce a hydroscopic mixture. Its low solubility is essential to the invention; this ensures that, in the gastrointestinal tract, the dipyridamole-containing particle is always surrounded by a sufficiently acidic microsphere in which the dipyridamole, which does not dissolve readily, is dissolved safely and completely.

If, for medical reasons, it is desirable to have a maximum blood level which is less in intensity but at the same time longer in duration, there are a number of pharmaceutical possibilities. As can be seen from Examples 1 and 2, an increase in the amount of acid added leads to acceleration in the release of dipyridamole, whereas a reduction (Example 2) slows down the release of active substance.

Other possible forms of dipyridamole granulates differ in that, in addition to readily water-soluble binders such as polyvinylpyrrolidinone, excipients which form a mucilage in the presence of water, or even water-repellent excipients, may be added to the dipyridamole and the acidic excipient. As can be seen from the results of the release of active substances in Examples 3 and 4, there is sometimes a significant delay in the release of active substance of up to about two hours.

If, on the other hand, a very rapidly rising blood level is required for the dipyridamole, it is particularly advantageous to change the type of acid used, as well as to increase the quantity of acid added or to reduce the particle size of the granulate, thus enlarging the surface area. Due to the high solubility of tartaric acid, citric acid, malic acid, and ascorbic acid, in particular, the dipyridamole dissolves completely in vitro in less than five minutes, irrespective of the pH of the medium of release (cf. Example 6).

Formulations of dipyridamole and acid may also be produced in tablet form surprisingly easily. It has been found that, even in the presence of conventional tablet-making excipients the compressing operation during tablet making is sufficient to achieve a sufficiently intimate mechanical combination of active substance and added acid. The examples relating to tablets containing 40 to 80 mg of tartaric acid and 75 mg of dipyridamole (Example 10) illustrate this, as do Examples 11 and 12 which contain 60 and 120 mg, respectively, of fumaric acid, with the same content of active substance (cf. Tables 1 and 2). For flavoring purposes, the tablets were all covered with a thin coating of hydroxypropyl methylcellulose. To improve the handling qualities, and to guard against hygroscopic behavior, coated tartaric acid was used in Example 10. Dissolution tests in vitro showed no significant differences between this product and non-coated tartaric acid.

It should be readily apparent to anyone skilled in the art that due to the nature and quantity of excipients added, the nature and quantity of acidic excipient, and the method of preparation (particle size of granulate), the release of the dipyridamole active substance can be controlled within wide limits to suit the medical requirements.

In addition to the conventional excipients used, namely, polyvinylpyrrolidone, hydrogenated castor oil, and polyacrylic acid, it is also possible to use excipients such as methylcellulose, ethylcellulose, hydroxyethylcellulose, or hydroxypropyl methylcellulose. Furthermore, to achieve the desired release, mixtures consisting of dipyridamole and acidic substances may be granulated with fats dissolved in organic solvents or with lacquers resistant to gastric juices such as cellulose acetate phthalate, shellac, and hydroxypropyl methylcellulose phthalate, and then compressed and broken up again into granules.

If, for therapeutic reasons, higher dosages of dipyridamole are required and high blood level peaks should be avoided because of possible side effects, these requirements are met, according to the invention, by the forms described in Examples 8 and 9. At dosages of more than 100 mg of dipyridamole, for example, these forms produce a maximum blood level of longer duration, instead of providing very high blood level peaks. Since these forms release the active substance in controlled manner, for example, over a period of from about 1 to 2 hours, the small particles are already located to a great extent in the duodenum, that is, in a pH range of over pH 4.0.

Therefore, these forms have to release the active substance in a pH medium in which the active substance is virtually no longer soluble, in the biological sense. If the release of dipyridamole is delayed any longer, that is, if the small units of dipyridamole pass into lower sections of the intestines, there is no longer any guarantee of total dissolution and absorption. The optimum absorption of dipyridamole is achieved, according to the invention, by accurately adapting the correlations between the nature and quantity of acidic excipient, the nature of the additives, and the method of processing to the release of active substance required.

In vivo testing of the forms according to the invention in man

All the tests were made on healthy volunteers, mostly in the form of cross-over tests. Since dipyridamole is only excreted in the urine to a very small extent, the only biological parameter used was the blood level, which was determined by measurement of fluorescence. The pharmaceutical forms prepared in Examples 1, 6, 8, 10, 11, and 12 were tested in adult males. However, since the oral pharmaceutical forms according to the invention without delayed release do not differ significantly from one another in vivo, the Figures only show the results pertaining to the forms of Examples 1, 6, and 8.

FIG. 1 shows the blood levels of 12 test subjects after the administration of 75 mg of dipyridamole solution, as well as after administration of a capsule prepared according to Example 1. It can be seen that after a short lag time, which was presumably caused by the dissolution of the capsule, substantially higher blood level values were obtained, on average, with the pharmaceutical forms of Example 1.

Figure 2:
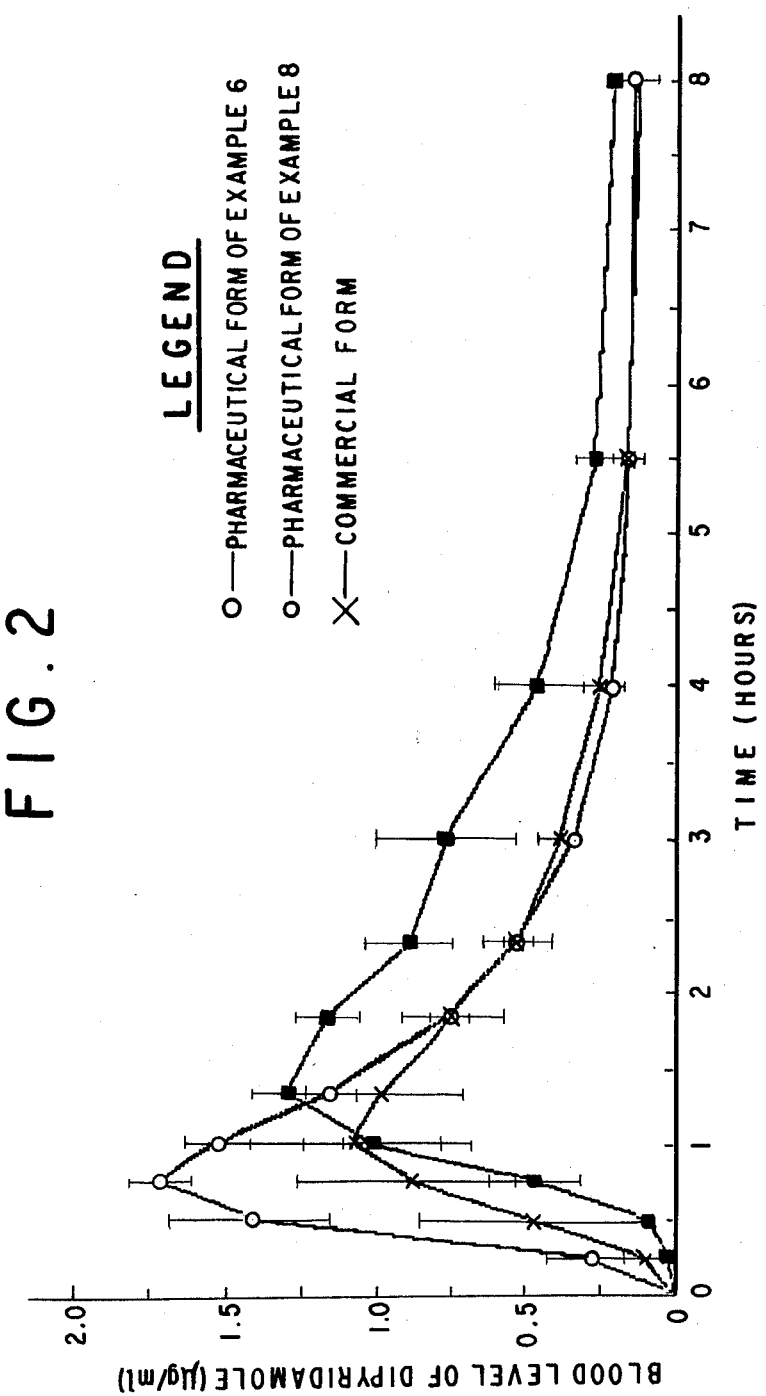
FIG. 2 represents a comparison of the release characteristics of two embodiments of the invention and of a known form for administering dipyridamole.

FIG. 2 shows that, with controlled release, the maximum blood levels achieved with a pharmaceutical form of Examples 6 and 8, each containing 75 mg of dipyridamole, are only slightly higher than the maximum blood level achieved with the current commercial form of administering dipyridamole, which form comprises 75 mg of active substance. However, with the forms of Examples 6 and 8 blood levels are maintained for a longer period of time, that is, dipyridamole may have a substantially longer lasting therapeutic effect in the form of the invention without any increase in the risk of side effects.

A study of the blood levels of three individual test subjects, represented by FIGS. 3A to 3C, shows that, particularly with low values for the commercial forms and in the case of a "non-absorber" (which occurs occasionally), there is a very sharp increase in the blood level (see FIG. 3A), whereas, in test subjects who showed a good blood level with the commercial forms, there is only a relatively smaller increase for pharmaceutical forms of Example 1 (see FIGS. 3B and 3C). Consequently, the usual fluctuations in blood level which make therapy difficult are reduced significantly. This is also shown by a comparison of the variation coefficients of the standard commercial form and a pharmaceutical form according to the invention (from Example 1) in Table 3 below. With the exception of the values after 0.25 hours (this value corresponding to dissolution of the capsule), the variation coefficients of the forms according to the invention are about 60% lower.

TABLE 3

Comparison of the variation coefficients of the standard commercial forms and a pharmaceutical form according to the invention

| Time (hrs.) | Variation coefficients (%)* | |
| --- | --- | --- |
| | Commercial form | Form of Example 1 |
| 0.25 | 92.4 | 141.1 |
| 0.50 | 120.9 | 45.0 |
| 0.75 | 63.2 | 15.8 |
| 1.00 | 59.6 | 17.0 |
| 1.33 | 58.1 | 18.5 |
| 1.83 | 54.7 | 20.7 |
| 2.33 | 55.4 | 23.3 |
| 3.00 | 50.6 | 31.0 |
| 4.00 | 60.6 | 31.0 |
| 5.50 | 61.4 | 43.6 |
| 8.00 | 61.6 | 28.1 |

*Standard through mean value

FIG. 4, shows that, with pharmaceutical forms of Example 6, blood levels corresponding to those of the current commercial form with 75 mg are obtained with a reduction in dosage from 75 mg to 50 mg, that is, a 33% reduction.

The following examples are intended to illustrate the invention and should not be construed as limiting the invention thereto.

EXAMPLES

Example 1

Three kilograms of dipyridamole were mixed with 6.3 kg of fumaric acid, and the mixture was moistened with 2 kg of a 15% alcoholic polyvinylpyrrolidone solution. After drying at 40° C. and screening, the granulate was mixed with 300 gm of polyvinylpyrrolidone powder and 100 gm of magnesium stearate. The mixture, compressed to form large tablets, was broken up in a dry granulation apparatus and screened. The fraction of granulate having particle sizes of from 0.4 to 1.0 mm was separated and was transferred into hard gelatin capsules.

The in vitro release of the active substance dipyridamole was tested under the following conditions:

| USP XX-paddle method, 100 revolutions per minute at 37° C. (unless otherwise stated, the in vitro release always occurred under these conditions) | |
|---|---|
| pH 1.2 | USP gastric juice |
| pH 4.0 | } McIlvain buffer |
| pH 6.0 | |

Amount of dipyridamole per capsule: 75 mg
The test results were as follows:

| | Release of Active Substance Dipyridamole | |
|---|---|---|
| pH Value | 50% | >90% |
| 1.2 | 3 min. | 8 min. |
| 4.0 | 4 min. | 12 min. |
| 6.0 | 5 min. | 15 min. |

Example 2

Forty-five kilograms of dipyridamole, 45 kg of fumaric acid, and 9 kg of polyvinylpyrrolidone were mixed for 20 minutes in a cube mixer. A quantity of 0.5 kg of magnesium stearate was added, and the mixture was agitated for a further five minutes. The mixture was then passed over a roller compactor, behind which a drying granulation apparatus with screening device was connected. The fraction having particle sizes of from 0.4 to 1.0 mm was used. Any finer particles were recycled and compressed again. The granulate separated was transferred, in the required dosage, into suitable hard gelatin capsules.

The in vitro release of the active substance dipyridamole was evaluated as in Example 1, and the test results were as follows:

| | Release of Active Substance Dipyridamole | |
|---|---|---|
| pH Value | 50% | >90% |
| 1.2 | 6 min. | 12 min. |
| 4.0 | 7 min. | 20 min. |
| 6.0 | 7 min. | 25 min. |

Example 3

Thirty kilograms of dipyridamole, 30 kg of fumaric acid, 29 kg of polyacrylic acid (available under the name Carbopol ®940 from B. F. Goodrich Chemical Co.), and 1 kg of magnesium stearate were made into a granulate according to the procedure described in Example 2. The test results, using the testing procedure of Example 1, were as follows:

| | Release of Active Substance Dipyridamole | |
|---|---|---|
| pH Value | 50% | >90% |
| 1.2 | 12 min. | 25 min. |
| 4.0 | 15 min. | 40 min. |

Example 4

A mixture of 2.5 kg of dipyridamole, 5.0 kg of fumaric acid, 1.3 kg of hydrogenated castor oil (available under the name Cutina ®HR from Henkel KGaA), and 0.1 of pyrogenic silicic acid (available under the name Aerosil ® from Degussa, Inc.) were made into a granulate according to the procedure described in Example 1. After the granulate was transferred into hard gelatin capsules, the in vitro release of the active substance dipyridamole was evaluated as in Example 1.

The test results were as follows:

| | Release of Active Substance Dipyridamole | | |
|---|---|---|---|
| pH Value | 50% | 75% | >90% |
| 1.2 | 28 min. | 65 min. | 105 min. |
| 4.0 | 34 min. | 72 min. | 123 min. |

Example 5

A quantity comprising 8.5 kg of dipyridamole was mixed with 9.0 kg of betaine hydrochloride, and the mixture was moistened with 2.2 kg of a 10% isopropanolic polyvinylpyrrolidone solution. After drying at 40° C. and screening, the granulate was mixed with 100 gm of magnesium stearate and 230 gm of pyrogenic silicic acid (Aerosil ®). The mixture was compressed to form tablets and broken up into granules; the fraction having particle sizes of from about 0.4 to 1.2 mm was used. After the granulate was transferred into hard gelatin capsules, the in vitro release of active substance dipyridamole was evaluated as in Example 1.

The test results were as follows:

| | Release of Active Substance Dipyridamole | |
|---|---|---|
| pH Value | 50% | >90% |
| 1.2 | 5 min. | 9 min. |
| 4.0 | 7 min. | 14 min. |

Virtually identical values were obtained when betaine hydrochloride was replaced by sodium hydrogen sulfate.

Example 6

Two hundred kilograms of tartaric acid in the form of spheroidal crystals with particle sizes of from about 0.5 to 0.8 mm were isolated in a rotary vessel with a 5% alcoholic solution of hydroxypropyl methylcellulose.

After moistening, in each case with a 10% alcoholic polyvinylpyrrolidone solution, a finely powdered mixture of dipyridamole: 8 parts
fumaric acid: 2 parts was sprinkled in until the pellets rolled freely again. After a short drying phase, adhesive solution was sprayed in again, and then further powder was added. A total of 150 kg of the powder mixture were added in this manner, about 75 kg of adhesive solution being required. The resulting dipyridamole-containing pellets had particle sizes of from about 0.6 to 0.9 mm and contained 33% of active substance and 64% of organic acid. After the final application of powder, the pellets were thoroughly dried.

The pellets were transferred in suitable dosage into hard gelatin capsules. Then, the in vitro release of active substance dipyridamole was evaluated as in Example 1. The test results were as follows:

| pH Value | Release of Active Substance Dipyridamole | |
|---|---|---|
| | 50% | >90% |
| 1.2 | 2 min. | 3 min. |
| 4.0 | 2 min. | 3 min. |
| 6.0 | 2 min. | 4 min. |

| pH Value | Release of Active Substance Dipyridamole | | | |
|---|---|---|---|---|
| | 25% | 50% | 75% | 90% |
| 1.2 | 19 min. | 40 min. | 63 min. | 87 min. |
| 4.0 | 17 min. | 35 min. | 64 min. | 90 min. |
| 5.0 | 14 min. | 30 min. | 55 min. | 85 min. |

As the starter cores it would also be possible to use small sugar pellets (nonpareils) or one of the following acids or substances of acid reaction: citric acid, ascorbic acid, malic acid, succinic acid, sodium hydrogen sulfate, betaine hydrochloride, or a monosodium or potassium salt of the above-mentioned polybasic organic acids.

It is possible to use as the acidic component of the powder mixture applied not only fumaric acid but any one of the above-mentioned substances of acid reaction, although fumaric acid, succinic acid, and betaine hydrochloride are preferred. It is also possible to use mixtures of these acidic substances.

The ratio of the mixture of dipyridamole and acidic-reacting component which is to be applied to the cores may also be, in addition to the value of 8:2 above, 10:0, 9:1, 7:3, 6:4, 5:5, 4:6, 3:7, 2:8, or 1:9. The quantity of powder mixture to be applied to the starter cores, may also be varied. However, care must be taken to ensure that the pellets contain at least 5 equivalents of acidic excipients to 1 mol of dipyridamole.

Example 7

In a fluidized bed granulator, 14 kg of dipyridamole, 0.5 kg of pyrogenic silicic acid (Aerosil ®), 0.7 kg of corn starch, 2.5 kg of polyethyleneglycol 6000 powder, and 25 kg of succinic acid were whirled around at 70° C. for two hours. After cooling, the mixture was passed through a 1.0 mm screen, 0.4% of magnesium stearate were added, and the resulting mixture was transferred into hard gelatin capsules.

The in vitro release of active substance dipyridamole was evaluated as in Example 1. The test results were as follows:

| pH Value | Release of Active Substance Dipyridamole | |
|---|---|---|
| | 50% | >90% |
| 1.2 | 9 min. | 18 min. |
| 4.0 | 12 min. | 22 min. |

It would also be possible to use fumaric acid, sodium hydrogen sulfate, or sodium hydrogen tartrate in place of succinic acid. The ratio of dipyridamole to acid or acidic salt may be kept within the limits specified, that is, at least five acid equivalents per mol of dipyridamole, by adjusting the composition of the mixture.

Example 8

A quantity of 1.9 kg of pellets containing dipyridamole as active substance and prepared according to Example 6 was sprayed with a 10% solution of hydroxypropyl methylcellulose phthalate (available under the name HP 55 ® from Shin-Etsu/Japan) in acetone/isopropanol (1:1) in a rapidly rotating coating vessel provided with baffle plates. Triacetin was added as plasticizer.

The in vitro release of active substance with a coating comprising 4% by weight, based upon the total weight of the coated pellet, was evaluated as in Example 1. The test results were as follows:

Example 9

A granulate was prepared from 5 kg of dipyridamole, 2.5 kg of polyethyleneglycol 6000 powder, 3 kg of fumaric acid, 2 kg of tartaric acid, and 0.3 kg of pyrogenic silicic acid (Aerosil ®). After screening, 0.2 kg of magnesium stearate were added, and the mixture was compressed to form 10 mm biconvex cores weighing 260 mg, that is, 100 mg of dipyridamole per core. After being thoroughly dusted, the cores were provided with a diffusion membrane in a coating pan. They were sprayed with a solution comprised of (1) methacrylic acid-methacrylic acid ester copolymer (Eudragit S ®, available from Röhm Pharma) and (2) hydroxypropyl methylcellulose phthalate (HP 55 ®)

in a ratio of 2:8 in acetone/isopropanol (1:1). In relation to the dry lacquer substance, 25% of polyethyleneglycol 6000 was added as plasticizer. Optionally, colored lacquer and/or talc could be added.

The in vitro release of active substance with a coating comprising 4% by weight, based upon the total weight of the coated tablets, was evaluated as in Example 1. The test results were as follows:

| pH Value | Release of Active Substance Dipyridamole | | | |
|---|---|---|---|---|
| | 25% | 50% | 75% | 90% |
| 1.2 | 25 min. | 44 min. | 68 min. | 95 min. |
| 4.0 | 30 min. | 48 min. | 74 min. | 105 min. |
| 6.0 | 27 min. | 39 min. | 54 min. | 77 min. |

Example 10

Coated dipyridamole tablets containing 80 mg of tartaric acid per tablet
Composition of 1 tablet:

| Component | Amount |
|---|---|
| Dipyridamole | 75 mg |
| Tartaric acid | 80 mg |
| Conventional tablet excipients | ad 250 mg |

Preparation:

The active substance was made into an aqueous granulate with the conventional tablet excipients, with the exception of lubricant. Lubricant and the tartaric acid coated with polyvinyl pyrrolidone and talc were added to the finished granulate to produce the finished mixture ready for compressing. From this mixture, round biconvex tablets with a diameter of 8 mm were produced. To mask the taste, these tablets were coated with hydroxypropyl methylcellulose.

Example 11

Coated dipyridamole tablets containing 60 mg of fumaric acid per tablet
Composition of 1 tablet:

| Component | Amount |
| --- | --- |
| Dipyridamole | 75 mg |
| Fumaric acid | 60 mg |
| Conventional tablet excipients | ad 195 mg |

Preparation:

The dipyridamole was mixed with fumaric acid and granulated under moist conditions. To the finished granulate were added the remaining excipients, which could be incorporated directly into tablets to form a finished mixture ready for compressing. From the resulting mixture, round biconvex cores 8 mm in diameter were compressed, and to mask the flavor, these cores were coated with hydroxypropyl methylcellulose in a coating vessel.

Example 12

Coated dipyridamole tablets containing 120 mg of fumaric acid per tablet

Composition of 1 tablet:

| Component | Amount |
| --- | --- |
| Dipyridamole | 75 mg |
| Fumaric acid | 120 mg |
| Conventional tablet excipients | ad 225 mg |

Preparation:

Analogously to the preparation of coated dipyridamole tablets containing 60 mg of fumaric acid according to Example 11.

Example 13

Coated dipyridamole tablets containing 60 mg of fumaric acid per tablet

Composition of 1 tablet:

| Component | Amount |
| --- | --- |
| Dipyridamole | 75.0 mg |
| Fumaric acid | 60.0 mg |
| Conventional tablet excipients | 60.0 mg |

Preparation:

Unlike the procedure of Example 11, dipyridamole was granulated with conventional tablet excipients. Fumaric acid and lubricant were added to this granulate to form a mixture ready for compressing. Further processing was effected analogously to Example 11.

Example 14

Coated dipyridamole tablets containing 60 mg of fumaric acid per tablet

Composition of 1 tablet:

| Component | Amount |
| --- | --- |
| Dipyridamole | 75.0 mg |
| Fumaric acid | 60.0 mg |
| Conventional tablet excipients | 60.0 mg |

Preparation:

As in Example 2, a dry granulate was prepared from 75 kg of dipyridamole, 60 kg of fumaric acid, and 60 kg of excipients (including polyvinyl pyrrolidone and magnesium stearate), which were incorporated directly into tablets to form a mixture ready for compressing. From this, cores with a diameter of 8.0 mm were compressed as in Example 11, and these cores were coated with a flavor-masking coating.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method of treating cardiovascular disorders in a host in need of such treatment which comprises administering to said host a cardiovascularly effective amount of an uncoated composition consisting essentially of (i) dipyridamole or an acid addition salt thereof and (ii) at least one pharmacologically acceptable acid or acid substance, the total amount of acid from acid addition salt present and acid or acid substance being in a ratio of at least about 5 acid equivalents to 1 mol of dipyridamole.

2. The method of claim 1, wherein the total amount of acid from acid addition salt present and acid or acid substance is in a ratio of from about 10 to 30 acid equivalents to 1 mol of dipyridamole.

3. The method of claim 1, wherein the pharmacologically acceptable acid or acid substance is selected from the group consisting of tartaric acid, citric acid, fumaric acid, succinic acid, malic acid, ascorbic acid, adipic acid, sodium or potassium salts of said acids, sodium or potassium hydrogen sulfate, betaine hydrochloride, anhydrides of succinic or glutaric acid which hydrolyse in water to form acids, D-glucuronic acid-γ-lactone, and mixtures thereof.

4. The method of claim 1 or 2, wherein the pharmacologically acceptable acid or acid substance is fumaric acid.

5. The method of claim 1, wherein the composition is in the form of granules.

6. The method of claim 5, wherein the granules have particle sizes of from about 0.1 to 2.0 mm.

7. The method of claim 6, wherein the granules have particle sizes of from about 0.25 to 1.25 mm.

8. The method of claim 5, wherein the granules are contained in hard gelatin capsules.

9. The method of claim 1, wherein the composition is in the form of pellets.

10. The method of claim 9, wherein the pellets have diameters of from about 0.1 to 2.0 mm.

11. The method of claim 10, wherein the pellets have diameters of from about 0.5 to 1.5 mm.

12. The method of claim 9, wherein the pellets are contained in hard gelatin capsules.

13. The method of claim 1, wherein the composition is in the form of tablets or tablet cores.

14. The method of claim 1, wherein the composition also comprises conventional pharmacological additives.

15. The method of claim 14, wherein the additives are selected from the group consisting of water-soluble binders, mucilaginous excipients, water-repellent excipients, and mixtures thereof.

16. The method of claim 15, wherein the additives are selected from the group consisting of methylcellulose, ethylcellulose, hydroxyethylcellulose, hydroxypropyl methylcellulose, polyacrylic acids, fats, and mixtures thereof.

17. The method of claim 1, wherein the composition is in the form of particles having a coating comprised of a lacquer which permits the release of at least 90% of the dipyridamole in the gastrointestinal tract over a period of two hours.

18. The method of claim 1, wherein the composition comprises tablet cores prepared by compressing granules consisting of dipyridamole or an acid addition salt thereof, acid or acid substance, lubricant, and other conventional additives to form uncoated tablet cores and then coating said uncoated tablet cores with a flavor-masking coating or a lacquer coating which permits the release of at least 90% of the dipyridamole in the gastrointestinal tract over a period of two hours.

19. The method of claim 1, wherein the composition comprises cores prepared by (a) moist or dry granulation of (i) dipyridamole or an acid addition salt thereof and (ii) acid or acid substance to form a granulate; (b) addition of further, conventional excipients to said granulate; (c) compression of said granulate to form uncoated cores; and (d) coating of said uncoated cores with a flavor-masking coating or a lacquer coating which permits the release of at least 90% of the dipyridamole in the gastrointestinal tract over a period of two hours.

20. The method of claim 1, wherein the composition comprises cores prepared by (a) moist or dry granulation of (i) dipyridamole or an acid addition salt thereof and (ii) conventional excipients to form a granulate; (b) addition of one or more acids or acid substances and lubricant to said granulate; (c) compression of said granulate to form uncoated cores; and (d) coating of said uncoated cores with a flavor-masking coating or a lacquer coating which permits the release of at least 90% of the dipyridamole in the gastrointestinal tract over a period of two hours.

21. The method of claim 18, 19, or 20, wherein the coating is a flavor-masking coating.

22. The method of claim 18, 19, or 20, wherein the coating is a lacquer coating which permits the release of the dipyridamole in the gastrointestinal tract over a period of two hours.

* * * * *

UNITED STATES PATENT AND TRADEMARK OFFICE
CERTIFICATE OF CORRECTION

PATENT NO. : 4,427,648

DATED : January 24, 1984

INVENTOR(S) : ROLF BRICKL et al.

It is certified that error appears in the above-identified patent and that said Letters Patent is hereby corrected as shown below:

Column 3, line 22, "said" should read -- acid --.

Signed and Sealed this

Twentieth Day of August 1985

[SEAL]

Attest:

DONALD J. QUIGG

Attesting Officer

Acting Commissioner of Patents and Trademarks